Figure 1:
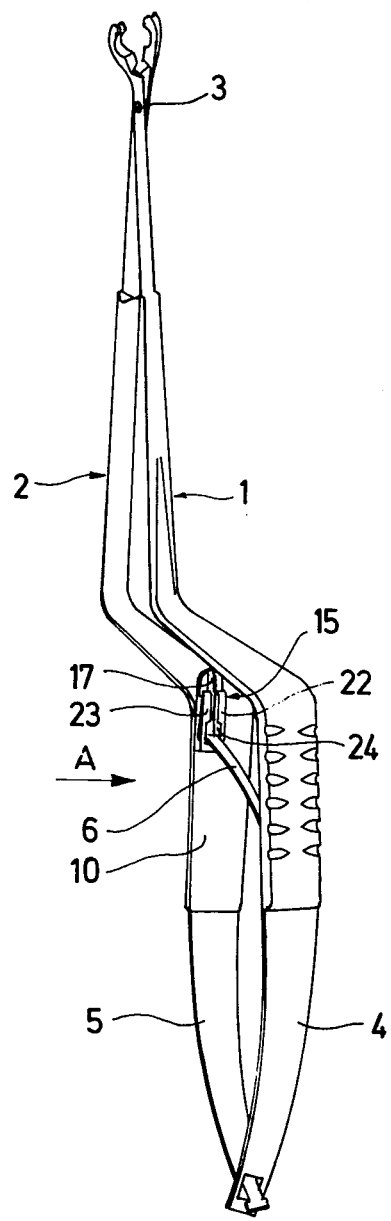

United States Patent [19]

Schwarz et al.

[11] Patent Number: 4,462,404
[45] Date of Patent: Jul. 31, 1984

[54] FORCEPS- OR TWEEZERS-SHAPED SURGICAL INSTRUMENT

[75] Inventors: Theodor Schwarz, Tuttlingen; Karl Freyer, Talheim; Manfred Theilmann, Tuttlingen, all of Fed. Rep. of Germany

[73] Assignee: Vormals Jetter & Scheerer Aesculap-Werke Aktiengesellschaft, Fed. Rep. of Germany

[21] Appl. No.: 341,747

[22] Filed: Jan. 22, 1982

[30] Foreign Application Priority Data

Jan. 31, 1981 [DE] Fed. Rep. of Germany ....... 3103352

[51] Int. Cl.³ ............................................ A61B 17/28
[52] U.S. Cl. ................................. 128/321; 128/322; 128/354; 81/313
[58] Field of Search ............... 128/354, 321, 322, 346, 128/325; 81/43, 336–338, 313; 294/99 S; 24/248 B; 227/DIG. 1 B; 433/159

[56] References Cited

U.S. PATENT DOCUMENTS

| | | | |
|---|---|---|---|
| 2,507,762 | 5/1950 | Drabik | 128/321 |
| 3,326,216 | 6/1967 | Wood | 128/325 |
| 3,393,680 | 7/1968 | Curutchet | 128/321 |

FOREIGN PATENT DOCUMENTS

| | | | |
|---|---|---|---|
| 1910127 | 10/1964 | Fed. Rep. of Germany | 128/318 |
| 430945 | 8/1967 | Switzerland | 128/346 |

OTHER PUBLICATIONS

Brochure AESCULAP Mikro– Neuro– and Vascular Surgery, 195–C (excerpts).
Drawing "Durchlaufsperre Japan-Modell".
Drawing "Schieberingsperre".

*Primary Examiner*—Michael H. Thaler
*Attorney, Agent, or Firm*—Kenway & Jenney

[57] ABSTRACT

Forceps have two branches movable opposite one another against a spring force and with a lock that fixes the distance between the branches. The lock engages as the two branches approach one another and is released by closing the branches further. This locking mechanism includes a locking arm mounted between the branches with a free end that rides between a sliding surface located on the inside wall of one of the branches and a guide member. The free end carries a locking element that engages a locking step formed on the sliding surface. The guide urges the locking element against the locking step and then, with a further closing movement of the branches, directs the locking arm free end to its initial, fully opened position. The guide has an enlarged opening that allows the free end to fall back onto the sliding surface.

18 Claims, 7 Drawing Figures

U.S. Patent   Jul. 31, 1984   Sheet 3 of 3   4,462,404

FORCEPS- OR TWEEZERS-SHAPED SURGICAL INSTRUMENT

This invention concerns a forceps- or tweezers-shaped surgical instrument as described in the specification of claim 1.

Such instruments are used in the surgical field in many ways, for example as pincers for applying clips, needle holders, and vascular clamps or with forceps of the most diverse designs. In all of these instruments, two branches can move elastically against one another, for example the two arms of a forceps or the branches of a tweezers-shaped instrument connected to one another at the ends by a pivot.

It is already known how to design such instruments so that they can be locked in a specific intermediate or closed condition.

For example, forceps for applying microclips to clamp off blood vessels are known in which a locking projection fastened to the inside wall of one branch passes through an opening in the other branch when the forceps are closed and locks behind it so that the forceps are locked in the closed position (AESCULAP brochure 195-C "Micro-, Neuro-, and Blood Vessel Surgery", 13th edition, April 1979). When the forceps are to be opened, the locking projection must be pushed back through the opening in the branch by finger pressure. In the case of tweezers, a so-called sliding ring lock is also known for fixing the separation of the two branches. For this purpose, one branch has a hook-shaped locking element extending away essentially perpendicular to the other, which locks behind the head of a pin fastened to the other branch. To release it, the tweezers are completely closed. The locking projections then slide on a ring mounted movably on the pin and carry this with them during the opening against the head of the pin in such a way that the hook-shaped locking elements can slide directly over the head of the pin when the ring is pulled back. Such systems are relatively complicated in structure and subject to problems when dirty, since it cannot then be guaranteed that the ring resting loosely on the pin can be pushed up to the head. However, this is a prerequisite for reliable operation.

In tweezers for applying clips, two spring locks have been attached to the insides of the branches for setting the mutual separation, one spring lock with a knife-shaped end and one spring lock with a V-shaped end whose vertex faces the other branch. Upon closing, the knife-shaped end of the one element slides past on one side of the V-shaped end of the other element and ultimately springs from the rear into the V-shaped end, so that the branches are secured against opening. When the tweezers are fully closed, the knife-shaped end again comes out of the V-shaped end and slides past the V-shaped end along the other side when the tweezers are then opened. With such a device, it is intrinsically possible to lock the instrument in a specific closed position when closing it, and to release the locking again only by further closing (cf. AESCULAP Company brochure 195-C "Micro-, Neuro-, and Blood Vessel Surgery", 13th edition). However, it is a drawback in this locking system that the two parts must be aligned very precisely to one another and reliable operation is no longer guaranteed even with a slight play when closing the instrument or with slight lateral bending of the branches. In the known locking systems, it is not possible to vary the particular fixed opening position, i.e., to lock the instrument in a smaller or a wider closed position if desired.

The purpose of this invention is to perfect a generic instrument in a structurally simple manner in such a way that a reliable locking of the separation of the two branches and a release of this locking by simply releasing the branches together is possible under all circumstances.

This problem is solved in an instrument of the type described initially pursuant to the invention by the features specified in the characterizing section of claim 1.

The design pursuant to the invention leads to the fact that upon closing, the locking element held on the elastic locking arm slides along between the guide on the one hand and the sliding surface of the other, with the locking element being pressed elastically against the sliding surface by the guide. As soon as the locking element jumps over the locking step, it locks on the shoulder formed by the locking step under the action of the elastic guide, and prevents the opening of the two branches. Upon further closing, the locking element is pushed further forward until it is released by the elastic guide. In the subsequent opening of the branches, the locking element slides on the guide and slides along the guide, on the side of the guide facing away from the sliding surface. The guide then constitutes a bridge which permits the locking element to slide over the locking step. Upon further opening, the locking element then springs down from the guide and again rests elastically on the sliding surface.

If the two branches are then closed again, the locking element enters the gap between the sliding surface and the guide so that the guide again pushes the locking element elastically against the sliding surface when it is pushed further forward.

In a preferred form of embodiment, it is provided that the locking arm is a leaf spring fastened on one end to the inside wall of one branch. It can then at the same time assume the task of pressing the two branches elastically away from one another so that the spring provided specifically for this purpose can be eliminated.

The locking element is preferably a pin extending laterally away from the free end of the locking arm.

It is also extraordinarily beneficial if the guide is composed of a leaf spring.

In a preferred example of embodiment of the invention, the guide is bent away in the closing direction beyond the locking step in the direction toward the sliding surface, with the bending of the guide preferably being only far enough beyond the locking step that the bent section of the guide presses the locking element in the locking position against the locking step opposite to the closing direction.

In a preferred example of embodiment, it is provided that the locking arm has a locking element projecting on two sides and a guide is located on each side of the locking arm. The two guides are preferably composed of two parallel blades which have a separation from one another at the section covering the locking step which is at least as large as the width of the locking arm but smaller than the width of the locking element, while in the section before the locking step in the closing direction it is larger than the width of the locking element. This guarantees that the locking element is pressed elastically against the sliding surface during the motion in the closing direction in the region in front of the locking step and in the region of the locking step itself, and that the locking element when moving in the direction of opening can again spring onto the sliding surface after sliding on the guide in the closing direction in front of the locking step.

It is desirable here if a longitudinal groove is provided in the sliding surface into which the free end of the locking arm extends, since the free end of the locking arm extending into the longitudinal groove is guided in this way against lateral shifting. It is beneficial here if the free end of the locking arm extending into the longitudinal groove in the sliding surface is bent towards the sliding surface. The locking element is preferably held to the end of the locking arm in the region of the bend.

The guide can be fastened to a step in the sliding surface located in front of the locking step in the closing direction whose height is greater than the height of the locking element. This ensures that the locking element can slide on the sliding guide when moving into the open position by spring pressure, and below the guide in the subsequent motion in the closing direction.

In a preferred example of embodiment of the invention, it is provided that the upper edge of the locking step projects compared to the rear step surface joining the two sliding surface regions. The projecting top edge then holds the locking element in its engaged position in direct contact with the step and prevents the locking element from springing back unintentionally to the upper section of the sliding surface.

It is particularly beneficial if at least one other locking step is located in the sliding surface before the locking step in the closing direction and if the guide also presses the locking element elastically against the sliding surface in the region of this other locking step. In this way, it is possible to lock the two branches at various distances, with each locking step corresponding to a specific separation of the branches. Basically, the sliding surface can have several such locking steps. The guide in such an example of embodiment extends from the last locking step in the closing direction across all of the locking steps, so that the locking element when moving in the opening direction slides on the guide over all of the locking steps and only then springs back to the sliding surface.

Another covered locking step can be located before the beginning of the guide in the closing direction, against which the locking element rests when the instrument is in the resting position under the action of a spring force pushing the branches apart from one another. The locking element and the locking arm then have the function of securing the two branches at a maximum distance and preventing further separation of the branches from one another.

In a preferred refinement, the locking arm can be lockable in various positions in the longitudinal branch direction at its point of fastening to the inside of the one branch, preferably by fastening the locking arm to the branch with a screw which passes through a longitudinal hole in the section of the locking arm resting against the inside wall of the branch. In this way, the opening of the two branches which results when the locking element engages behind the locking step of the sliding surface can be continuously adjusted by varying the fastening of the locking arm in the longitudinal direction of the branch.

To prevent a pivoting of the locking arm with respect to the inside of the branch, it can be provided that a longitudinal groove is located in the inside wall of the branch on which the locking arm is held, into which a projection of the locking arm projects. This projection constitutes protection against rotation.

As mentioned previously, the securing system pursuant to the invention can be used for all forceps- or tweezers-shaped surgical instruments whose branches are pushed apart from one another by spring force. For example, with tweezers for applying clips which have such a mechanism, it is possible to hold the clips in the tweezers for applying clips in an only slightly opened position, with the latter assuming a fixed open position because of the locking system. The clip held becomes completely open only when the operating site is reached, by pressure on the forceps. At the same time, the locking mechanism of the two branches is thereby unlocked, so that in the subsequent opening of the branches, the clip is released and the clip tongs can open completely.

The opening of the clip tongs in the locked position can be selected so that the clips are not completely opened, contrary to previously known tongs, so that the clips are treated gently and in particular, the clips are prevented from losing their stretching force.

Figure 2:
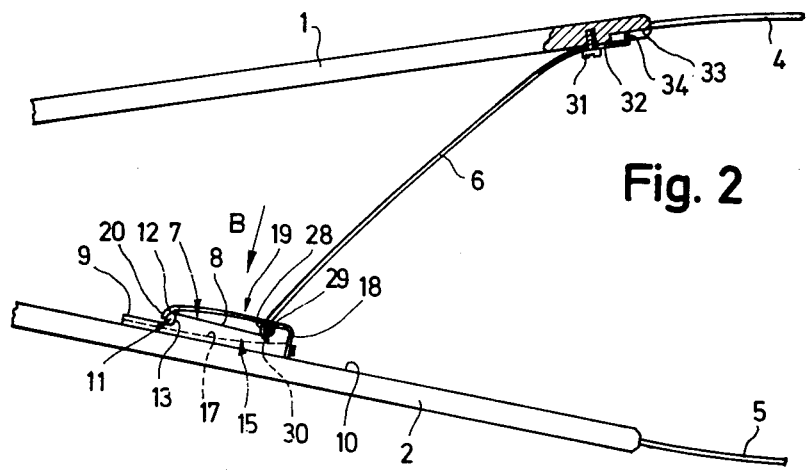
Figure 3:
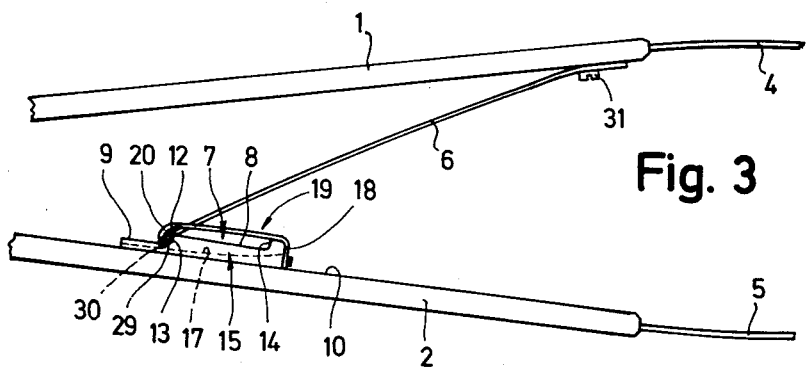
Figure 4:
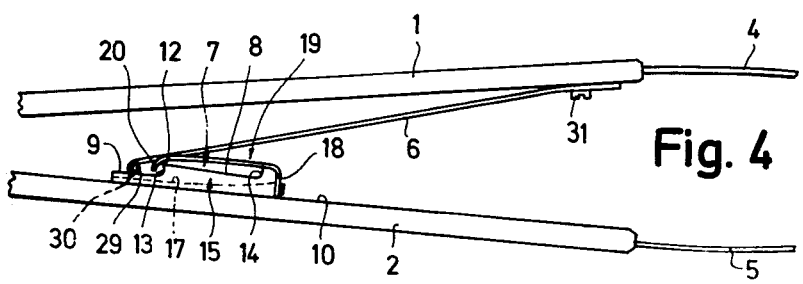
Figure 5:
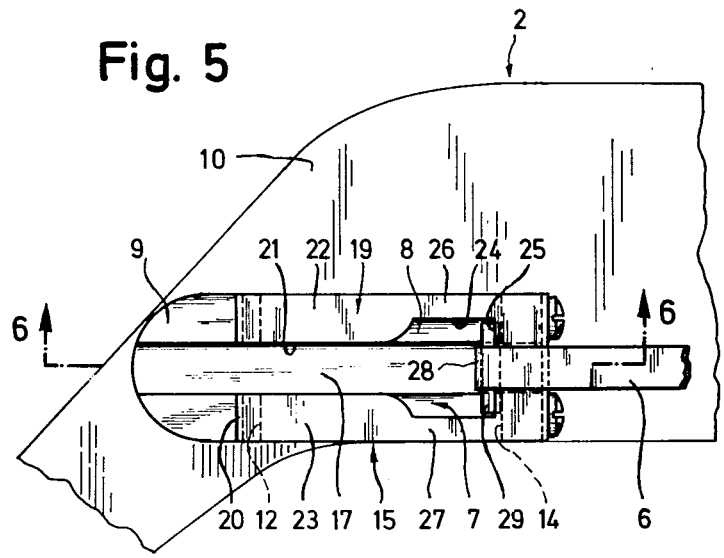
Figure 6:
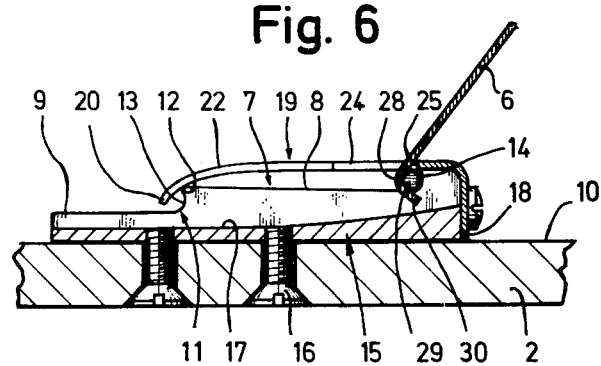

The following description of the preferred embodiments of the invention together with the drawing, is intended for a more detailed explanation. The drawing shows:

FIG. 1 a view of tweezers for applying clips with a lock pursuant to the invention;

FIG. 2 a partial side view of tweezers in the open position in the direction of the arrow A in FIG. 1;

FIG. 3 a view similar to FIG. 2 of tweezers in a locked intermediate position;

FIG. 4 a view similar to FIG. 2 of tweezers in the completely closed position;

FIG. 5 a partial view of the lock pursuant to the invention in the direction of the arrow B in FIG. 2;

FIG. 6 a sectional view along the line 6—6 in FIG. 5, and

Figure 7:
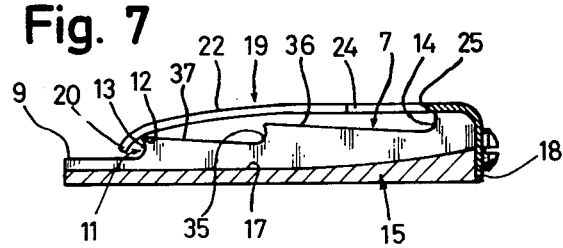

FIG. 7 a longitudinal sectional view of a section of a modified example of embodiment of a lock pursuant to the invention.

The invention will be explained below with the use of tweezers for applying clips, which are used to bring clips into position for clamping off blood vessels. It is understood that the invention can also be used for other forceps- and tweezer-shaped surgical instruments.

The tweezers for applying clips illustrated in FIG. 1 have two arms or branches 1 and 2 which can pivot with respect to one another by means of a connection 3. At the forward ends, the two branches are formed as tweezers to hold a clip not shown in the drawings, and the ends of the two branches are designed as spring arms 4 and 5 which interpenetrate at the end and are bent overall in such a way that they press the two branches away from one another. Because of the force of these spring arms, the tweezers are in the open position at rest.

To lock the two branches in a partially closed position, a locking mechanism is provided which comprises an elongated thin leaf spring 6 attached to the inside of one branch and a sliding surface 7 fastened to the inside wall of the opposite branch. The construction of these parts will be described below in detail with the use of the illustration of FIGS. 2 through 6.

The sliding surface 7 is divided into an upper surface 8 and a lower surfce 9, both of which run essentially parallel to the inside wall 10 of the branch holding the sliding surface. The upper surface 8 has a greater distance from the inside wall 10 then the lower surface 9, and in the transition region of the two partial surfaces they form a locking step 11 which has an essentially circular arc-shaped cross section in its vertical region, so that the upper edge 12 of the locking step projects in a horizontal direction beyond the rear wall 13 of the step (FIG. 6). Another step 14 is located at the end of the upper surface 8, which has a similar form in cross section to that of the locking step 11.

The described sliding surface is defined by a sliding body 15, which is fastened to the branch by screws 16, for example (FIG. 6). This sliding body 15 has a central longitudinal groove 17 which divides the entire sliding surface 7 into two halves (FIG. 5). The purpose of this longitudinal groove 17 will be described below in detail.

The vertically bent end 18 of a leaf spring 19 is fastened to the rear of the sliding body 15, and the spring extends essentially parallel to the upper surface 8. Its free end 20 bent in the direction of the sliding surface terminates just beyond the locking step 11. In the area of the step 14, the distance of the leaf spring 19 from the upper partial surface 8 is determined by the height of the step 14, while the leaf spring in the resting state rests against the upper edge 12 of the locking step 11, as can be seen from the illustration of FIG. 6.

The leaf spring 19 is divided into two blades 22 and 23 by a gap 21 essentially covering the longitudinal groove 17, with the gap running from the free end 20 of the leaf spring 19 to a broadened, elongated opening 24. The opening 24 is located above the upper surface 8 in the region before the step 14 and is arranged so that its edge 25 facing the step 14 slightly overlaps the step 14 (cf. FIG. 6).

The opening 24 is wider than the gap 21, so that the two blades 22 and 23 are connected to the end of the leaf spring 19 held on the sliding body by narrow bridges 26 and 27.

The leaf spring 6 held on the other branc constitutes a locking arm, to whose free end 28 is fastened a locking pin 29 projecting out on both sides. The leaf spring is bent around this locking pin 29 in the direction of the other branch and forms a tab 30 projecting approximately perpendicular to the leaf spring.

The locking arm formed by the leaf spring is fastened to the one branch by means of a screw 31 which passes through a longitudinal hole 32 arranged in the longitudinal direction at the fixed end of the leaf spring 6. To prevent rotation of the leaf spring on the branch, the branch has a longitudinal groove 33 into which extends the end of the leaf spring 6 bent towards the branch. The width of the longitudinal groove 33 corresponds to the width of the end 34 projecting into it.

The leaf springs are arranged on the two branches in such a way that the locking pin carried by the free end of the leaf spring slides on the two halves of the sliding surface 7 with its two laterally projecting sections when the tweezers are closed, i.e., when the branches are approaching one another (cf. FIG. 2). The width of the longitudinal groove 17 of the sliding body 15 corresponds essentially to the width of the tab 30 on the free end of the leaf spring 6 which extends into the longitudinal groove 17 when the locking pin moves along the sliding surface, and thus guides the free end of the leaf spring relative to the sliding body. The width of the gap between the two blades 22 and 23 is at least as great as the width of the leaf spring 6 in this region, so that the leaf spring can be pushed between the two blades without hindrance. However, the gap is less wide than the locking pin 29 at the free end of the leaf spring 6. On the other hand, the opening 24 is wider than this locking pin 29.

The method of operation of the lock pursuant to the invention will be described below with the use of FIGS. 2 through 4.

In the open position, the tweezers are in the position illustrated in FIG. 2. The two branches are pushed apart from one another by the spring arms 4 and 5, so tht the locking pin 29 is drawn towards the step 14. In this position, the locking pin is fixed by the leaf spring 19 whose edge 25 extends beyond the step 14 towards the front. Consequently, the leaf spring 6 secured at its free end between the leaf spring 19 and the sliding surface 7 at the step 14 limits the opening of the tweezers.

By pressing the two branches together, the free end of the leaf spring 6 with the locking pin 29 is pushed along the upper surface 8 in the closing direction, with the locking pin 29 sliding at the end of the opening 24 away from the step 14 beneath the two blades 22 and 23 of the leaf spring 19 and being pressed elastically against the upper surface 8 of the sliding surface 7 by these blades which form a guide during the further advance. It is essential for this purpose that the distance of the leaf spring 19 at the beginning of the blades 22 and 23 from the upper partial surface be greater than the height of the locking pin.

In the further advance of the locking pin in the closing direction, the locking pin finally jumps over the locking step 11 to the lower partial surface 9 and is pressed against the rear wall of the locking step 11 by the bent free end 20 of the leaf spring 19. The locking pin is fixed in this position, since it can no longer reach the upper surface because of the projecting upper edge 12 of the locking step 11 and because of the force of the leaf spring 19. The tweezers are therefore now locked in an intermediate position (FIG. 3).

In pressing the branches further together, the locking pin is shifted on the lower partial surface 9 farther into the closed position, while it bends the ends of the leaf spring 19 elastically backward and slides forward beneath this leaf spring. The tweezers can now be moved into the maximum shut position, with the locking pin reaching its forwardmost position on the sliding surface 7 (FIG. 4).

When the distance between the branches is then again increased under the influence of the two spring arms 4 and 5, the locking pin finally reaches the bent free end 20 of the leaf spring 19 and slides onto the two blades 22 and 23, since the distance of the front edge of the leaf spring 19 from the lower surface 9 is smaller than the height of the locking pin. During the further opening, therefore, the locking pin slides over the side of the blades 22 and 23 away from the sliding surface, which thus constitute a guide for the locking pin, until the locking pin snaps elastically onto the upper surface 8 in the region of the opening 24. In the further opening, the locking pin 29 again finally reaches the initial position illustrated in FIG. 2, described above, in which the tweezers are opened to the maximum.

In this way it is possible to close the tweezers without producing a locking in an intermediate position if the tweezers are closed until the locking pin comes out of the gap between the leaf spring 19 and the sliding surface (FIG. 4). However, if the tweezers are closed only until the locking pin engages behind the locking step 11 (FIG. 3), the tweezers remain in this open position, which can be selected, for example, so that in this position a clip is held but only slightly opened, so that it can be introduced into the operating area in this position. To release the lock, it suffices to close the tweezers further briefly and then to open them again.

The exact position of the maximum open position and the central locking position can be chosen by shifting the fixed end of the leaf spring 6 along the branch. This is possible continuously because of the longitudinal hole 32.

Various modifications of the preferred example of embodiment decribed with the use of FIGS. 1 through 6 are possible. For example, the upper surface can be divided into several partial surfaces 36 and 37 subdivided in each case by another locking step 35, as illustrated in FIG. 7. In this example of embodiment also, the leaf spring 19 covers the entire upper surface up to just beyond the lowest locking step. In this way, two fixed intermediate positions can be occupied. Of course, it is also possible to divide the sliding surface into partial surfaces by a larger number of locking steps and thus to provide a number of possible intermediate positions.

In the examples of embodiment illustrated, the leaf spring 6 constituting a locking arm is arranged in such a way that the locking pin (locking element) is shifted in the direction towards the closing of the branches; this is not absolutely necessary. It would also be possible to attach the leaf spring 6 to the opposite branch in such a way that the free end is shifted in the opposite direction while closing the tweezers. In such a design, the entire sliding body would be positioned on the opposite branch, rotated by 180°.

The design of the locking arm as a leaf spring with suitable dimensions would also make it possible to dispense with the spring arms 4 and 5 pushing the two branches apart from one another, since the leaf spring 6 shows the same action.

The locking arm does not necessarily have the form of a leaf spring. For example, it would also be possible to link the locking arm with the ability to pivot on the inside of one branch, and by means of a compression spring against the inside wall of the opposite branch, and thus to press against the sliding surface located there.

We claim:

1. Forceps- or tweezers-shaped surgical instrument with two branches movable opposite one another against the action of an elastic restoring force and with a lock for fixing the mutual distance between the branches which becomes active during the approach of the two branches and can be released by still further approach, characterized by the fact that a locking arm (6) is fastened to the inside of one branch with its free end (28) resting elastically against the inside of the other branch and sliding along the branch (2) in the closing direction during the approach of the two branches (1, 2) and along its inner wall during the separation of the two branches in the direction of opening, that the locking arm (6) carries a locking element (29) projecting laterally at its free end (28), that a sliding surface (7) for the locking element (29) is located on the inside wall (10) of the opposite branch (2) in the sliding region of the end of the locking arm (28), the sliding surface has a locking step (11) running across the direction of motion of the locking element, and dropping off in the direction of closing, that a guide (19, 22, 23) arranged essentially parallel to the sliding surface (7) is coordinated with the sliding surface and presses the locking element (29) elastically against the sliding surface (7) at least in the region of the locking step (11), that the guide (22, 23) terminates beyond the locking step (11) in the closing direction, so that the locking element (29) reaches in front of the guide (22, 23) upon the further approach of the branches (1, 2), that in the rest position the end (20) of the guide (22, 23) in front of the locking step (11) has a separation from the sliding surface (7) which is smaller than the height of the locking element (29), so that the locking element (29) slides on the guide (22, 23) when moving in the direction of opening by enlarging the separation of the branches, and that the guide (22, 23) terminates beyond the locking step (11) in the opening direction and at that point has a distance from the sliding surface (7) in the rest position that is greater than the height of the locking element (29), so that the locking element (29), when moving in the opening direction after sliding on the guide (22, 23) beyond the locking step (11), springs onto the sliding surface (7) and enters the gap between the sliding surface (7) and the guide (22, 23) in the subsequent motion in the closing direction.

2. Instrument pursuant to claim 1, characterized by the fact that the locking arm is a leaf spring (6) fastened at one end to the inner wall of one branch (1).

3. Instrument pursuant to claim 1, characterized by the fact that the locking element is a locking pin (29) projecting laterally from the free end (28) of the locking arm (6).

4. Instrument pursuant to claim 1, characterized by the fact that the guide is composed of a leaf spring (19, 22, 23).

5. Instrument pursuant to claim 1, characterized by the fact that the guide (22, 23) is bent towards the sliding surface (7) after the locking step (11) in the direction of closing.

6. Instrument pursuant to claim 5, characterized by the fact that the bending of the guide (19, 22, 23) is only so far beyond the locking step (11) that the bent section (20) of the guide (19, 22, 23) presses the locking element (29) in the locked position towards the locking step (11) opposite to the direction of closing.

7. Instrument pursuant to claim 1, characterized by the fact that the locking arm (6) carries a locking element (29) projecting on two sides and a guide (22, 23) is located on each side of the locking arm (6).

8. Instrument pursuant to claim 7, characterized by the fact that the two guides are composed of two parallel blades (22, 23) which have a distance from one another in the sections covering the locking step (11) which is at least as great as the width of the locking arm (6) but smaller tha the width of the locking element (29), while the distance in the section lying in front of the locking step (11) in the closing direction is greater than the width of the locking element (29).

9. Instrument pursuant to claim 1, characterized by the fact that a longitudinal groove (17) is provided in the sliding surface (7), into which the free end (28, 30) of the locking arm (6) extends.

10. Instrument pursuant to claim 9, characterized by the fact that the free end (28) of the locking arm extending into the longitudinal groove (17) of the sliding surface (7) is bent towards the sliding surface (7).

11. Instrument pursuant to claim 10, characterized by the fact that the locking element (29) is held on the end of the locking arm (28) in the region of the bending of the end of the locking arm (28).

12. Instrument pursuant to claim 1, characterized by the fact that the guide (19, 22, 23) is fastened to a step

(14) in the sliding surface (7) lying in front of the locking step (11) in the closing direction whose height is greater than the height of the locking element (29).

13. Instrument pursuant to claim 1, characterized by the fact that the upper edge (12) of the locking step (11) projects beyond the rear face of the step (13) connecting the two sliding surface regions (8, 9).

14. Instrument pursuant to claim 1, characterized by the fact that at least one other locking step (35) is located in the sliding surface (7) before the locking step (11) in the closing direction and that the guide (19, 22, 23) also presses the locking element (29) elastically against the sliding surface (7) in the region of these other locking steps (35).

15. Instrument pursuant to claim 1, characterized by the fact that another covered locking step (14) is located in front of the beginning of the guide (22, 23) in the closing direction, against which the locking element (29) rests when the instrument is in the rest position under the effect of a spring force pushing the branches (1, 2) apart from one another.

16. Instrument pursuant to claim 1, characterized by the fact that the locking arm (6) can be fixed at its point of fastening at the inside of the one branch (1) at various positions in the longitudinal direction of the branch.

17. Instrument pursuant to claim 16, characterized by the fact that the locking arm (6) is fastened by a screw (31) to the branch (1), which passes through a slot (32) in the section of the locking arm (6) resting against the inside wall of the branch.

18. Instrument pursuant to one of the claims 16 or 17, characterized by the fact that a longitudinal groove (33) is located in the inside wall of the branch on which the locking arm (6) is held, into which a projection (34) of the locking arm (6) extends.

* * * * *